United States Patent
Bose et al.

(10) Patent No.: US 6,835,848 B1
(45) Date of Patent: Dec. 28, 2004

(54) ONE-POT SYNTHESIS OF ALKYL 3-CYCLOPROPYLAMINO-2-[2,4-DIBROMO-3-(DIFLUROMETHOXY) BENZOYL]-2-PROPENOATE AS A USEFUL INTERMEDIATE FOR ANTIBACTERIAL QUINOLONE MEDICAMENTS

(75) Inventors: Prosenjit Bose, Haryana (IN); Naresh Kumar, Haryana (IN); Taro Kiyoto, Toyama (JP)

(73) Assignees: Ranbaxy Laboratories Limited, New Delhi (IN); Toyama Chemical Co., Ltd., Tokyo (JP)

( * ) Notice: Subject to any disclaimer, the term of this patent is extended or adjusted under 35 U.S.C. 154(b) by 205 days.

(21) Appl. No.: 10/221,113

(22) PCT Filed: Mar. 7, 2001

(86) PCT No.: PCT/IB01/00316

§ 371 (c)(1),
(2), (4) Date: Jan. 6, 2003

(87) PCT Pub. No.: WO01/66512

PCT Pub. Date: Sep. 13, 2001

(30) Foreign Application Priority Data

Mar. 7, 2000 (IN) ........................................ 196/Del/2000

(51) Int. Cl.[7] ........................ C07C 229/00; C07C 65/32; C07C 59/56

(52) U.S. Cl. ............................ 560/37; 560/39; 560/43; 560/47; 560/48; 562/459; 562/472

(58) Field of Search ............................ 560/37, 39, 43, 560/47, 48; 562/459, 472

(56) References Cited

U.S. PATENT DOCUMENTS 5,935,952 A    8/1999   Todo et al. ............... 514/230.2

FOREIGN PATENT DOCUMENTS

| EP | 1132375 A1 | 9/2001 |
| JP | 06-016642 | 1/1994 |
| WO | WO 99/21849 | 5/1999 |

OTHER PUBLICATIONS

Cecchetti, V. et al., "Potent 6–Desfluoro–8–methylqunolones as New Lead Compounds in Antibacterial Chemotherapy," *J. Med. Chem.* 1996: 39; 4952–4957.

Primary Examiner—Cecilia J. Tsang
Assistant Examiner—Taylor V. Oh
(74) Attorney, Agent, or Firm—Jayadeep R. Deshmukh, E

(57) ABSTRACT

The present invention relates to a new and industrially advantageous one-pot process for the preparation of alkyl 3-cyclopropyl amino-2-[2,4-dibromo-3-(difluoromethoxy) benzoyl]-2-propenoates of in which R represents methyl or ethyl, which are valuable intermediates for the production of highly active antibacterial quinolone medicaments.

9 Claims, No Drawings

US 6,835,848 B1

ONE-POT SYNTHESIS OF ALKYL 3-CYCLOPROPYLAMINO-2-[2,4-DIBROMO-3-(DIFLUROMETHOXY) BENZOYL]-2-PROPENOATE AS A USEFUL INTERMEDIATE FOR ANTIBACTERIAL QUINOLONE MEDICAMENTS

FIELD OF THE INVENTION

The present invention relates to a new and industrially advantageous one-pot process for the preparation of alkyl 3-cyclopropyl amino-2-[2,4-dibromo-3-(difluoromethoxy) benzoyl]-2-propenoates in which R represents methyl or ethyl, which are valuable intermediates for the production of highly active antibacterial quinolone medicaments.

BACKGROUND OF THE INVENTION

A previously known general method for the synthesis of intermediate, alkyl 3-cyclopropyl amino-2-[2,4-dibromo-3-(difluoromethoxy) benzoyl]-2-propenoate of the following formula:

FORMULA I

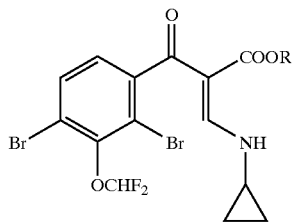

has been reported in U.S. Pat. No. 5,935,952 assigned to Toyama Chemical Company Ltd. The general method described in this patent includes, reaction of the compound of the following formula:

FORMULA II

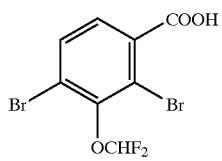

with a halogenating agent such as thionyl chloride to obtain acid chloride of the following formula:

FORMULA III

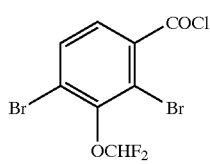

which on reaction with metal salt of malonic ester of the following formula:

Na/KOOCCH$_2$COOR                  FORMULA IV wherein R is the same as defined above, in the presence of magnesium chloride at a temperature of about 45° C. Decarboxylation of Formula IV affords a compound of the following formula:

FORMULA V

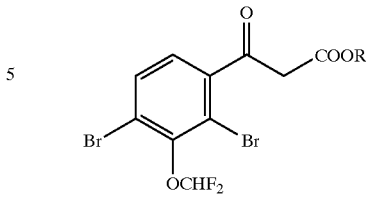

in which R is as defined above. Reaction of the compound of Formula V with an acetal such as N,N-dimethylformamide dimethyl acetal, N,N-dimethylformamide diethyl acetal to give a compound of the following formula:

FORMULA VI

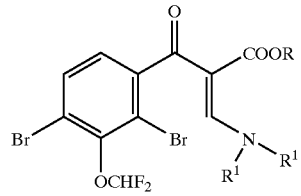

wherein $R_1$ is methyl or ethyl, which on reaction with cyclopropylamine gives the intermediate, methyl/ethyl 3-cyclopropyl amino-2-[2,4-dibromo-3-(difluoromethoxy) benzoyl]-2-propenoate, of Formula I.

The above mentioned method described in the prior art for the manufacture of the compound of Formula I suffers from the following limitations and for various reasons stated below are not suitable for commercial purposes.

The process is lengthy involving six steps.

The process generates a lot of effluent waste and hence is not eco-friendly.

SUMMARY OF THE INVENTION

It is an object of the present invention to solve the problems associated with the prior art and to provide an efficient method.

According to one aspect of the present invention there is provided a one-pot process for the preparation of alkyl 3-cyclopropylamino-2-[2,4-dibromo-3-(difluoromethoxy) benzoyl]-2-propenoate of Formula I. The process provides obvious benefits with respect to economics and convenience to operate at a commercial scale.

More particularly, the present invention relates to a process for the preparationofalkyl3-cyclopropylamino-2-[2,4-dibromo-3-dfluoromethoxy) benzoyl]-2-propenoate of Formula I, wherein R is methyl or ethyl comprising reacting 2,4-dibromo-3-(difluoromethoxy)benzoic acid of Formula II, with a halogenating agent to get a corresponding acid chloride of Formula III, which on reaction with ester of 3,3-dialkyl amino acrylate of the following formula:

FORMULA VII

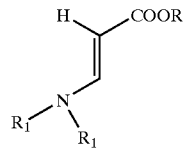

wherein $R_1$ is methyl or ethyl, in a suitable solvent in the presence of an organic base to give alkyl-3,3- dialkylamino2[2,4-dibromo-3-difluoromethoxy) benzoyl]-2-ropenoate of Formula VI wherein R and R₁ are methyl or ethyl which on treatment with cyclopropylamine affords the product of Formula I, and R is the same as defined above. More particularly, the compound of Formula II is reacted with thionyl chloride to provide an acid chloride of Formula III following a process known in the prior art. The acid chloride is then reacted with methyl/ethyl ester of 3,3-dimethyl/diethylamino acrylate of Formula VI (R and R₁ are methyl or ethyl) in a suitable solvent in the presence of an organic base at a selected temperature within the range of 40–80° C., preferably, 50–70° C. during a period of one to several hours. The suitable solvent is selected from the group comprising of aromatic solvents, chlorinated solvents ester solvents and mixture(s) thereof. Preferably, the solvents are selected from the group comprising benzene, toluene, xylenes, chloroform, dichloroethane, dichloromethane methyl acetate, butyl acetate, ethyl acetate or mixture(s) thereof. The suitable organic base is selected from the group comprising triethylamine, trimethyl amine, picolines, pyridine and pyridine derivatives. The reaction mixture is then cooled and poured into water. The organic layer contains the compound of Formula VI wherein R₁ is methyl or ethyl and is taken as such for reaction with cyclopropylamine at a selected temperature within the range of 0–30° C., preferably 5–10° C. for 0.5 to several hours. The desired compound methyl/ethyl 3-cyclopropylamino-2[2,4-dibromo-3-(difluoromethoxy) benzoyl]2-propenoate of Formula I is isolated by conventional methods.

In the following section a preferred embodiment is described by way of an example to illustrate the process of this invention. However, this is not intended in any way to limit the scope of the present invention.

DETAILED DESCRIPTION OF THE INVENTION

Example 1

Preparation of Ethyl-3-cyclopropylamino-2-(2,4-dibromo-3-difluoromethoxy) benzoyl]-2-propenoate.

To a mixture of 2.4-dibromo-3-(difluoromethoxy) benzoic acid (10 g) and thionyl chloride (4.38 gm) was added a mixture of toluene (15 ml) and N,N-dimethyl formamide (0.2 ml). The reaction mixture was heated slowly to reflux and stirred at reflux for about 2.5 hours. The reaction mixture was then cooled to 35° C. and added a solution of ethyl 3,3-dimethylaminoacrylate (4.13 gm), and triethylamine (3.79 gm) in toluene (20 ml) drop-wise during a period of about 1 hour maintaining a temperature of 35–40° C. After the addition was over, the reaction temperature was slowly increased to 60–65° C. and stirred the reaction mixture for about 24 hours. Cooled the reaction mixture to 30° C., added water (20 ml) and stirred for about 10 minutes. The organic layer was separated, cooled to about 5° C. and cyclopropylamine (1.82 gm) was added to it drop-wise maintaining temperature at 8–10° C. during a period of about 10 minutes. Stirred the reaction mixture for about 2 hours, solvent was removed under vacuum (~80% of the original amount) and cooled the reaction mixture to about 20° C. The solid separated was filtered and dried to afford ethyl 3-cyclopropylamino-2-[2,4-dibromo-3 (difluoromethoxy) benzoyl]-2-propenoate (10 gm).

While the present invention has been described in terms of its specific embodiments, certain modifications and equivalents will be apparent to those skilled in the art and are intended to be included within the scope of the present invention.

Example 2

Preparation of ethyl 3-cyclopropylamino-2-[2,4-dibromo-3-(difuluoromethoxy)benzoyl]2-propenoate To a mixture of 2,4-dibromo-3-(difluoromethoxy)benzoic acid (50 g) in ethyl acetate (175 mL) was added N,N-dimethyl formamide (1 mL) and thionyl chloride (18.1 g). The reaction mixture was heated to reflux and stirred at reflux for 1 hr. After evaporation of ethyl acetate, (125 mL), triethylamine (16.1 g) and ethyl 3,3-dimethylaminoacrylate (20.7 g) were added to the reaction mixture at room temperature. This reaction mixture was heated to reflux and stirred at reflux for 3 hrs. The mixture was then cooled to 25° C., water (100 mL) was added and the mixture was stirred for about 10 minutes. The organic layer was separated and cyclopropylamine (9.9 g) was added to it and the reaction mixture was stirred at 25° C. for 1 hr. The solvent of the reaction mixture was exchanged by isopropanol (200 mL), maintaining the temperature about 68° C. The crystallization was achieved by cooling of the mixture, followed by filtration, washing with isopropanol and drying to afford ethyl3-cyclopropylamino-2-[2,4-dibromo-3-(difuluoromethoxy)benzoyl]-2-propenoate (58.6 g).

We claim:

1. A process for the preparation of alkyl 3-cyclopropylamino-2-[2-4-dibromo-3-(difluoromethoxy) benzoyl]-2-propenoate of the following formula:

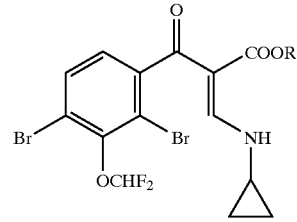

FORMULA I wherein R is methyl or ethyl, comprising reacting 2,4-dibromo-3(difluoromethoxy) benzoic acid of the following formula:

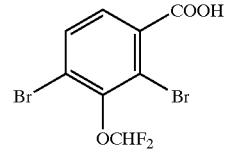

FORMULA II with a halogenating agent to get a corresponding acid chloride of the following formula:

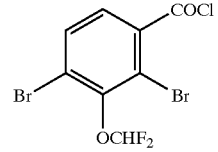

FORMULA III which on reaction with alkyl ester of 3,3-dialkyl amino acrylate of the following formula:

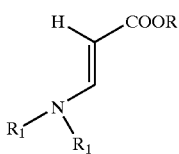

FORMULA VII wherein $R_1$ is methyl or ethyl in a suitable solvent in the presence of an organic base, to give alkyl 3,3-dialkylamino-2-[2,4-dibromo3(difluoromethoxy)benzoyl]-2-propenoate of the following formula:

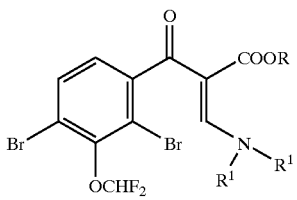

FORMULA VI wherein R and $R_1$ are methyl or ethyl wherein R and $R_1$ are the same as defined above, which on treatment with cyclopropylamine affords the product of Formula I.

2. The process of claim 1 wherein the halogenating agent is thionyl chloride.

3. The process of claim 1 wherein the alkyl ester of 3,3-dialkylaminoacrylate is methyl ester of 3,3-dimethylaminoacrylate.

4. The process of claim 1 wherein the alkyl ester of 3,3-dialkylamino acrylate is ethyl ester of 3,3-diethylamino acrylate.

5. The process of claim 1 wherein the solvent is selected from a group comprising aromatic solvents, chlorinated solvents, ester solvents and mixture(s) thereof.

6. The process of claim 5 wherein a solvent is selected from the group comprising benzene, toluene, xylenes, chloroform, dichloromethane, dichloroethane methyl acetate, butyl acetate, ethyl acetate and mixture(s) thereof.

7. The process of claim 1 wherein the organic base is selected from the group comprising triethylamine, trimethylamine, picoline(s), and pyridine.

8. The process of claim 1 wherein the reaction temperature is in the range of 40–80° C.

9. The process of claim 8 wherein the reaction temperature is in the range of 50–70° C.

* * * * *

UNITED STATES PATENT AND TRADEMARK OFFICE
CERTIFICATE OF CORRECTION

PATENT NO.   : 6,835,848 B1                                                            Page 1 of 1
DATED        : December 28, 2004
INVENTOR(S)  : Bose et al.

It is certified that error appears in the above-identified patent and that said Letters Patent is hereby corrected as shown below:

<u>Title page, Item [54] and Column 1, line 3,</u>
Title, "(DIFLUROMETHOXY)" should read -- (DIFLUOROMETHOXY) --

<u>Title page,</u>
Item [57], ABSTRACT,
Line 4, "-propenoates of in which" should read -- -propenoates in which --.

<u>Column 2,</u>
Line 50, "preparationofalkyl3-" should read -- preparation of alkyl 3- --
Line 51, "dfluoromethoxy" should read -- difluoromethoxy --

<u>Column 3,</u>
Line 1, "dialkylamino2[" should read -- dialkylamino-2[ --
Line 2, "ropenoate" should read -- propenoate --
Line 41, "2.4-" should read -- 2,4- --

<u>Column 4,</u>
Line 4, "difuluoromethoxy" should read -- difluoromethoxy --
Line 25, "difuluoromethoxy" should read -- difluoromethoxy --
Line 44, "dibromo-3(" should read -- dibromo-3-( --

<u>Column 5,</u>
Line 12, "dibromo3)" should read -- dibromo-3-( --

Signed and Sealed this

Tenth Day of May, 2005

JON W. DUDAS
*Director of the United States Patent and Trademark Office*